United States Patent [19]

Abdulla

[11] 4,411,753

[45] Oct. 25, 1983

[54] SYNTHESIS OF 6-T-ALKYL-3-PYRIDAZINONES

[75] Inventor: Riaz F. Abdulla, Greenfield, Ind.

[73] Assignee: Eli Lilly and Company, Indianapolis, Ind.

[21] Appl. No.: 366,882

[22] Filed: Apr. 8, 1982

[51] Int. Cl.³ ............................................ C07D 237/14
[52] U.S. Cl. ................................. 204/158 R; 544/239; 549/478
[58] Field of Search ................... 544/239; 204/158 N; 549/478

[56] References Cited

U.S. PATENT DOCUMENTS 4,152,517  5/1979  Levinson et al. .................. 544/239

FOREIGN PATENT DOCUMENTS 2017136  10/1971  Fed. Rep. of Germany ...... 544/239
2435244   7/1974  Fed. Rep. of Germany .
2445681   9/1974  Fed. Rep. of Germany .
2640806   3/1977  Fed. Rep. of Germany ...... 544/239

*Primary Examiner*—Donald G. Daus
*Assistant Examiner*—G. M. Hendricks
*Attorney, Agent, or Firm*—Joseph A. Jones; Arthur R. Whale

[57] ABSTRACT

A class of 6-t-alkyl-3-pyridazinones are prepared from 3-t-alkanoyl-2-propenoic acids by irradiation with strong light and reaction with hydrazine.

12 Claims, No Drawings

SYNTHESIS OF 6-T-ALKYL-3-PYRIDAZINONES

BACKGROUND OF THE INVENTION

1. Field of the Invention

This invention belongs to the field of synthetic organic chemistry, and provides a process for preparing 6-t-alkyl-3-pyridazinones which are useful intermediates for N-pyridazinylbenzamide herbicides. The tertiary alkyl group of the compounds is quite bulky and has a strong steric effect, which impedes or, in some cases, substantially prevents the closure of the pyridazine ring by conventional methods.

2. State of the Art

The formation of 3-pyridazinones from 3-acyl-2-propenoic acids and hydrazine is a known process. It is quite effective for preparing compounds wherein the acyl group is benzoyl or the like, as shown by West German application No. 2,435,244. When the acyl group is a tertiary alkanoyl group, however, the cyclization does not go smoothly to form the desired pyridazinone, but instead gives a complex product, believed to be a dipyrazolopyrimidinedione.

SUMMARY OF THE INVENTION

This invention provides a process for preparing a pyridazinone of the formula

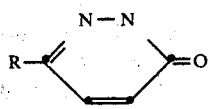

wherein
R is of the formula

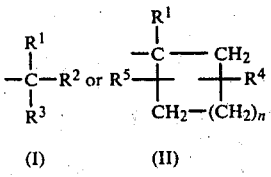

$R^1$ is $C_1$–$C_4$ alkyl;
$R^2$ and $R^3$ are independently $C_1$–$C_{13}$ alkyl, or halo-$C_1$–$C_{13}$ alkyl;
n is 0–4;
$R^4$ and $R^5$ are independently hydrogen, halo or $C_1$–$C_4$ alkyl;
comprising irradiating a 2-propenoic acid of the formula

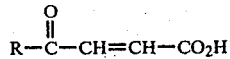

to form a furanone of the formula

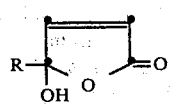

and reacting the furanone with hydrazine.

DESCRIPTION OF THE PREFERRED EMBODIMENTS

In this document, all temperatures are described in degrees Celsius.

The general chemical terms in the description above have their usual meanings in organic chemistry. For example, the term $C_1$–$C_4$ alkyl includes such groups as methyl, ethyl, propyl, isopropyl, butyl, s-butyl and t-butyl. $C_1$–$C_{13}$ alkyl includes the groups just mentioned, as well as such larger groups as pentyl, heptyl, undecyl, dodecyl, tridecyl, neopentyl, 1-methylbutyl, 2-ethylbutyl, 3-methylbutyl, 4-methylhexyl, 2,2-diethylpentyl, 3-propylhexyl, 1,3-diethylpentyl, 2-methyloctyl, 3-propyloctyl, 4-ethylheptyl, 2-butylheptyl, 3-methyldecyl, 1-ethylundecyl, 2,4-diethylnonyl, 1-pentylhexyl, 5-propyldecyl and the like.

The halo-$C_1$–$C_{13}$ alkyl groups of the compounds prepared by this invention include $C_1$–$C_{13}$ alkyl groups as described above substituted with chlorine, bromine and fluorine atoms in any desired manner, from a single halogen atom on the alkyl group up to and including full halogen substitution. Exemplary haloalkyl groups are further illustrated below.

Similarly, the halogen atoms which may constitute the $R^4$ and $R^5$ substituents of the compounds may be chlorine, bromine or fluorine atoms.

It will be seen that the tertiary alkyl groups of the compounds may be simple groups where the adjacent carbon atom is substituted with 3 alkyl (or haloalkyl) groups, or two of the groups may combine to form a cycloalkyl group, which may optionally be substituted. The cycloalkyl groups may be of from 3 to 7 carbons, as defined by the integer n in the formula above.

Although it is believed that the nature of the 3-pyridazinones prepared by this invention is entirely clear, a group of representative products will be mentioned to assure the reader's understanding.

6-(6,6,6-trifluoro-1-methyl-1-propylhexyl)-3-pyridazinone
6-[2-(2,2-dibromoethyl)-1-ethyl-1-methylbutyl]-3-pyridazinone
6-(1-butyl-3-chloro-1-ethylhexyl)-3-pyridazinone
6-(1-s-butyl-3-fluoro-1-pentylheptyl)-3-pyridazinone
6-[1-(3,3-dichloro-1-ethylbutyl)-1-ethyl-3-methylhexyl]-3-pyridazinone
6-[4,5,5-trichloro-2-ethyl-1-(1-ethylpropyl)-1-methylpentyl]-3-pyridazinone
6-(1-ethyl-3,3,4-trifluoro-1-hexyloctyl)-3-pyridazinone
6-[1-(2-ethylbutyl)-1-isopropyl-4-trifluoromethylheptyl]-3-pyridazinone
6-[3-bromo-1-butyl-3-ethyl-1-(1-ethylbutyl)hexyl]-3-pyridazinone
6-(9-bromo-1-heptyl-1-methylnonyl)-3-pyridazinone
6-[3,3-difluoro-1,5-dimethyl-1-(5-methylhexyl)heptyl]-3-pyridazinone
6-[6-chloro-1-(2-ethylpentyl)-1-ethyl-2-propylhexyl]-3-pyridazinone
6-[6-bromo-1-isopropyl-1-(1-propylbutyl)-decyl]-3-pyridazinone
6-(1-t-butyl-10,10,10-trifluoro-1-octyldecyl)-3-pyridazinone
6-[5-chloro-1-methyl-2-propyl-1-(1-propylpentyl)heptyl]-3-pyridazinone
6-[2-butyl-2,3-dichloro-1-(4-ethylhexyl)-1-isopropylhexyl]-3-pyridazinone
6-[5,5,6,6-tetrabromo-1-s-butyl-1-(3-methylnonyl)undecyl]-3-pyridazinone 6-(1-[4-(3-chloropropyl)heptyl]-1-isopropyldecyl)-3-pyridazinone
6-[1-(2-butylpentyl)-1-propyl-6-trifluoromethyldecyl]-3-pyridazinone
6-[12,12,12-trichloro-1-isopropyl-1-(3-propylhexyl)-dodecyl]-3-pyridazinone
6-(1-[2-(5,5-dibromopentyl)hexyl]-1-propylundecyl)-3-pyridazinone
6-[1-(2-butylhexyl)-7-(2-fluoroethyl)-1-methyldecyl]-3-pyridazinone
6-[2-butyl-7,7-dichloro-1-(2,4-diethylhexyl)-1-methyloctyl]-3-pyridazinone
6-[2,2-dichloro-1-(1,5-dimethylhexyl)-1-methyltridecyl]-3-pyridazinone
6-[1-[4-(3,3,4,4,4-pentafluorobutyl)octyl]-1-methyldodecyl]-3-pyridazinone
6-[8,8,8-trifluoro-1-methyl-2-pentyl-1-(1-pentylhexyl)octyl]-3-pyridazinone
6-[14-bromo-1-methyl-1-(2,6-dimethylnonyl)-tetradecyl]-3-pyridazinone
6-[1-(1,4-dibromo-2,5-diethylnonyl)-1-ethyltridecyl]-3-pyridazinone
6-[2-bromo-5-chloro-2-pentyl-1-propyl-1-(2-pentylheptyl)nonyl]-3-pyridazinone
6-(1,2,4,8-tetramethyl-1-propyldecyl)-3-pyridazinone
6-(1,1-dimethyltetradecyl)-3-pyridazinone
6-(2-butyl-1-isobutyl-1-methyldecyl)-3-pyridazinone
6-(1,1-diethyl-5-pentylundecyl)-3-pyridazinone
6-(11-methyl-1-pentyl-1-propyldodecyl)-3-pyridazinone
6-(1-chloromethyl-1-ethyl-3-methylpentyl)-3-pyridazinone
6-[1-isobutyl-1-(2-fluoroethyl)-2-ethylbutyl]-3-pyridazinone
6-[1-(2,2-dibromopropyl)-1-methylheptyl]-3-pyridazinone
6-[1-(4-bromobutyl)-1-t-butyl-3-ethylpentyl]-3-pyridazinone
6-[1-(1-chloromethylpropyl)-1-ethyl-2-propylbutyl]-3-pyridazinone
6-(1-pentachloroethyl-1-isopropyloctyl)-3-pyridazinone
6-[1-(2,2,3-tribromobutyl)-1-ethyl-6-methylheptyl]-3-pyridazinone
6-[1-(5-fluoropentyl)-3-ethyl-1-methylhexyl]-3-pyridazinone
6-[1-(2,2-dichloropentyl)-1-methyl-2-propylpentyl]-3-pyridazinone
6-[1-(2,2-dibromopropyl)-6,6,6-trifluoro-1-methylhexyl]-3-pyridazinone
6-(1-[1-(2,2-dibromoethyl)propyl]-5-bromo-1-ethylpentyl)-3-pyridazinone
6-(1-[1-chloromethyl)propyl]-2-fluoro-1-isopropyl-3-methylpentyl)-3-pyridazinone
6-(1-pentachloroethyl-3-chloro-1-propylhexyl)-3-pyridazinone
6-[1-(3,4,4-tribromobutyl)-1-s-butyl-3-fluoroheptyl]-3-pyridazinone
6-[1-(3,3-dichloro-2-ethylbutyl)-6-fluoro-1-methylhexyl]-3-pyridazinone
6-(2,2-dibromo-1-[1-(1,1,2-trichloropropyl)-propyl]-1-ethylhexyl)-3-pyridazinone
6-(3,3,4-trifluoro-1-methyl-1-octyloctyl)-3-pyridazinone
6-[1-methyl-1-(2-propylpentyl)-4-trifluoromethylheptyl]-3-pyridazinone
6-[3-bromo-2-ethyl-1-(3-ethylhexyl)-1-methylhexyl]-3-pyridazinone 6-[8-bromo-1-methyl-1-(3-methylnonyl)nonyl]-3-pyridazinone
6-[1-(1,1-difluoro-4-methylhexyl)-1-methyldecyl]-3-pyridazinone
6-[3-butyl-1-(5-chloro-2-propylpentyl)-1-methylhexyl]-3-pyridazinone
6-[6-bromo-1-methyl-1-(3-propylhexyl)decyl]-3-pyridazinone
6-(1-decyl-10,10,10-trifluoro-1-methyldecyl)-3-pyridazinone
6-[3-butyl-1-(4-chloro-3-propylhexyl)-1-ethylheptyl]-3-pyridazinone
6-[1-(1-butyl-1,4-dichloropentyl)-1,3,5-triethylheptyl]-3-pyridazinone
6-[9,9,10,10-tetrabromo-1-(1,3-dimethylhexyl)-1-methylundecyl]-3-pyridazinone
6-(1-[3-(2-chloropropyl)heptyl]-1-methyldodecyl)-3-pyridazinone
6-[6-trifluoromethyl-1-methyl-1-(1-pentylhexyl)decyl]-3-pyridazinone
6-[3,3,4-trichloro-1-methyl-1-(2,6-dimethylnonyl)-dodecyl]-3-pyridazinone
6-(1-[2-(5-bromopentyl)hexyl]-1-ethyltridecyl)-3-pyridazinone
6-[1-ethyl-7-(2-fluoroethyl)-1-(2-pentylheptyl)decyl]-3-pyridazinone
6-[1-(1-butyl-4,5-dichloroheptyl)-1-isopropyl-2,3,4-trimethyldecyl]-3-pyridazinone
6-[1-(12,12-dichlorododecyl)-1-methyltetradecyl]-3-pyridazinone
6-(3-butyl-1-[2-(1,1,2,2-tetrafluorobutyl)-octyl]-1-methyldecyl)-3-pyridazinone
6-[5-pentyl-1-(2,2,3-trifluoro-1-pentylheptyl)-1-propylundecyl]-3-pyridazinone
6-[12-bromo-1-(6-methylundecyl)-1-methyltetradecyl]-3-pyridazinone
6-(2,6-dibromo-1-chloromethyl-4,8-diethyl-1-methyldecyl)-3-pyridazinone
6-[2-bromo-4-chloro-1-(1-fluoroethyl)-1-methyl-2-pentylnonyl]-3-pyridazinone
6-(1,2-dimethylcyclopropyl)-3-pyridazinone
6-(3-t-butyl-1-ethyl-2-fluorocyclobutyl)-3-pyridazinone
6-(2-chloro-4-ethyl-1-propylcyclopentyl)-3-pyridazinone
6-(2-bromo-4-butyl-1-isopropylcyclohexyl)-3-pyridazinone
6-(1-butyl-3-methyl-4-isopropylcycloheptyl)-3-pyridazinone
6-(1-t-butyl-3-s-butyl-2-ethylcyclopentyl)-3-pyridazinone
6-(1-s-butyl-2-isopropyl-3-propylcyclohexyl)-3-pyridazinone
6-(1,4-diisobutyl-3-propylcycloheptyl)-3-pyridazinone
6-(2-isobutyl-1-methylcyclobutyl)-3-pyridazinone
6-(2-bromo-4-s-butyl-1-ethylcyclopentyl)-3-pyridazinone
6-(4-butyl-3-chloro-1-ethylcyclohexyl)-3-pyridazinone
6-(3-t-butyl-5-fluoro-1-methylcycloheptyl)-3-pyridazinone Certain classes of products of this invention are preferred. The following group of definitions describes the preferred classes; it will be understood that the definitions below may be combined as desired to provide additional preferred classes.

a. Compounds wherein R is of formula I;
b. Compounds of formula I wherein $R^2$ is $C_1-C_4$ alkyl or halo-$C_1-C_4$ alkyl;

c. Compounds of formula I wherein $R^3$ is $C_1$-$C_4$ alkyl or halo-$C_1$-$C_4$ alkyl;
d. Compounds of formula I wherein $R^2$ is $C_1$-$C_4$ alkyl;
e. Compounds of formula I wherein $R^3$ is $C_1$-$C_4$ alkyl;
f. Compounds of formula I wherein $R^1$ is not branched;
g. Compounds of formula I wherein $R^2$ is not branched;
h. Compounds of formula I wherein $R^3$ is not branched;
i. Compounds wherein R is of formula II;
j. Compounds of formula II wherein n is 2-4;
k. Compounds of formula II wherein n is 3;
l. Compounds of formula II wherein $R^4$ and $R^5$ are the same;
m. Compounds of formula II wherein $R^4$ and $R^5$ are hydrogen.

The 2-propenoic acids which are the starting compounds for the process of this invention are obtainable by methods commonly understood by organic chemists. A particularly convenient method for preparing them is indicated in the preparations below, and proceeds, in general, as follows.

In the first step, the methyl ester of the carboxylic acid corresponding to the R group, of the formula R—$CO_2CH_3$, is reacted with acetonitrile in the presence of sodium hydride to prepare a tertiary alkanoyl acetonitrile, of the formula

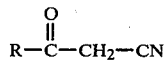

The above substituted acetonitrile is then reacted with hydrochloric acid of from about 6 N to about 12 N concentration, to prepare the corresponding methyl ketone by hydrolytic decarboxylation. The ketone is of the formula

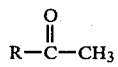

The above step is the subject of an application titled Synthesis of Acetyl-t-alkanes, filed on the same day with this application by the present inventor.

The ketone is then reacted with chloral (trichloroacetaldehyde) or its hydrate in acetic acid and heated under reflux to prepare a keto alcohol intermediate of the formula

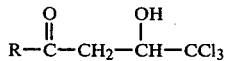

Finally, the keto alcohol is hydrolyzed with base in aqueous ethanol to prepare the starting compound of the present process. It should be noted that, in some preparations of the 2-propenoic acid, the keto alcohol is not fully dehydrated and a mixture is obtained, containing some part of the keto-hydroxy acid

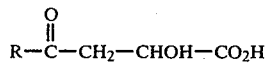

The presence of the keto-hydroxy acid is not a disadvantage, because it dehydrates to form the 2-propenoic acid under the conditions of the process of this invention and proceeds to the desired product.

The Preparations below illustrate the above-described steps.

The process of this invention proceeds in two steps, which may be carried out in the same mixture. In the first step, the 2-propenoic acid is irradiated with strong light to cyclize it to the furanone shown above. A chemist can also think of the cyclization as being an isomerization, since the 2-propenoic acid form of the compound may be termed its E-isomer and the furanone, its Z-isomer.

The irradiation is carried out with the starting compound in a solvent, which, of course, should not be an ultraviolet absorber. Thus, aromatic solvents are not appropriate, but ethers, alcohols, haloalkanes, alkanes and esters may conveniently be used as solvents. Applicant prefers ethers, including especially diethyl ether, tetrahydrofuran, diisopropyl ether and the like. Other suitable solvents, including such as ethanol, methanol, isopropanol, butanol, dichloromethane, 1,2-dichloroethane, 1,1,2-trichloroethane and the like are useful. Further, esters such as ethyl acetate, methyl propionate and the like and amides such as dimethylformamide and dimethylacetamide are useful solvents in the process.

The light source used in the irradiation step is not critical. Light of wave lengths in the ultraviolet range is believed to be particularly appropriate. The process has been carried out successfully with an ordinary sun-lamp as the light source, and in bright sunlight. In general, the light source should provide a substantial amount of light in the wavelength range of about 100 to 1000 m$\mu$. As usually is the case with light-induced reactions, the cyclization step may be conveniently carried out by flowing the solution of the starting compound in a thin film past the light source, in order to use the light energy most efficiently. The step may be carried out, however, quite satisfactorily in an ordinary flask or vessel equipped to allow the entrance of light energy.

The irradiation of the starting 2-propenoic acid is carried out until the desired degree of completion of the reaction has been obtained. As is normally the case, it may be more or less advantageous, in a given circumstance, to press the cyclization to its maximum yield. If it is desirable in the circumstances to use the starting compound to the utmost, then it will be advantageous to continue the irradiation for a relatively long period of time to maximize yield. On the other hand, it may be more advantageous to maximize the throughput of product from the equipment, in which case the irradiation should be relatively brief, and the percentage yield of the process will be less.

The temperature at which the irradiation step is carried out is not important. Any convenient temperature in the range of, for example, from about 0° to about 100° is satisfactory. Of course, the temperature must be high enough to keep the starting compound in solution. Temperatures above the boiling point may be used if the process step is carried out under pressure.

The pyridazinone is formed by reacting the furanone with hydrazine. The reaction is very quick and efficient. No excess amount of hydrazine or furanone is needed, as the reaction has been found to be substantially quantitative. A moderate excess may be used and will have no adverse results. It would be preferable, of course, to use excess hydrazine, if any excess is to be used, since hydrazine is abundant and cheap compared to the furanone.

The temperature of the reaction with hydrazine is unimportant; again, temperatures in the range of from about 0° to about 100° may be used as convenient. Higher or lower temperatures may be used, if the necessary precautions are taken to avoid freezing or evaporation.

While it is preferred simply to add the hydrazine to the irradiation reaction mixture, it is entirely possible to isolate the furanone and start the hydrazine reaction with a fresh reaction mixture.

The hydrazine reaction is carried out in the presence of a mineral acid and, preferably, a lower alkanol. The preferred mineral acid is hydrochloric acid. Sulfuric acid, phosphoric acid, polyphosphoric acid and the like are also useful. The concentration of the acid is not critical, but chemists will understand that sulfuric acid and the various phosphoric acids should be diluted with water to the general range of about 25–50%.

It is most preferred to carry out the reaction in the presence of ethanol. Other lower alkanols such as methanol, propanol, isobutanol and the like may also be used as reaction solvents. Ethers and aromatics have quite low solvency for the starting compounds but may be used as reaction solvents if the concentration is low. The reaction may also be run without a solvent if desired, using hydrazine and the mineral acid as the reaction solvent.

The acid should be present in a substantial molar excess relative to the amount of the furanone and of hydrazine. An excess in the range of 3X or more is adequate; larger amounts of acid are not harmful. When the reaction with hydrazine is carried out in a fresh reaction mixture, it is preferred to use an alkanol, most preferably ethanol, as the solvent. Alternatively, a complex solvent system may be used in which an alkanol is a major constituent, making up about one-third or more of the volume of the mixture. When the hydrazine reaction is carried out in the irradiation reaction mixture, some alkanol should be added along with the hydrazine and acid, in order to prepare a solvent system in which the alkanol makes up about one-third or more of the total volume of the mixture.

Further, the pyridazinone can be prepared by combining the two steps. The 2-propenoic acid and hydrazine are combined in the presence of mineral acid in an alkanolic solvent as described above, and the mixture is then irradiated as described above. The acid is cyclized to the furanone form, which reacts with the hydrazine substantially as quickly as it is formed. An example below is illustrative.

The pyridazinone which is the product of the present invention is obtained in the form of its acid addition salt, because of the acid in the reaction mixture, and may be isolated as such or converted to the free base by simple contact with a strong base, as is usually done with such salts.

The pyridazinone which is the product of this invention is most preferably used as an intermediate in the synthesis of a series of herbicidal N-pyridazinylbenzamides which are taught in U.S. patent application Ser. No. 302,323, of Burow. The herbicides are of the formula

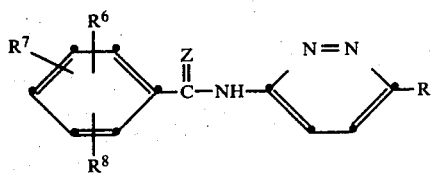

wherein Z is oxygen or sulfur;

$R^6$ is hydrogen, halogen, $C_1$–$C_4$ alkyl, or $C_1$–$C_4$ alkoxy;

$R^7$ is hydrogen, halogen, $C_1$–$C_4$ alkyl, $C_1$–$C_4$ alkoxy, $C_1$–$C_4$ alkylthio or trifluoromethyl;

$R^8$ is hydrogen, halogen, $C_1$–$C_4$ alkyl, $C_1$–$C_4$ alkoxy or $C_1$–$C_4$ alkylthio; provided that when one of $R^6$, $R^7$ or $R^8$ is alkyl, one or both of the other phenyl substituents is other than hydrogen; and when $R^7$ is trifluoromethyl, one or both of $R^6$ and $R^8$ is other than hydrogen.

The products of the process of this invention are transformed to the herbicidal benzamides in a simple step-wise process. The pyridazinone is reacted with a chlorinating agent such as phosphorus oxychloride to replace the oxo with chlorine, is aminated with ammonia under pressure to prepare the 4-aminopyridazine, and is finally reacted with the appropriate benzoyl (or thiobenzoyl) compound to form the herbicidal benzamide.

Synthesis of the benzamides is further explained in the preparations below.

The benzamide herbicides are used in agriculture as herbicides have often been used in the past. Many of them are so active that application rates in the range of from about 0.1 to about 2 kg. per hectare are adequate. In general, they are used at rates from about 0.05 to about 15 kg. per hectare. When the compounds are used for post-emergence control of weeds, higher application rates, such as from about 1 to about 20 kg. per hectare, are preferred.

It is not necessary to incorporate the herbicides in the soil. The compounds are more potent when incorporated than when applied on the surface of the soil, however, and incorporation is therefore preferred. The compounds are effective when applied either before or after the emergence of weeds; the pre-emergence use of them is more effective and is accordingly preferred. The compounds are effective against a wide range of undesirable vegetation, including most of the herbaceous weeds and grasses which afflict agriculture. Accordingly, the herbicidal benzamides are widely usable.

The benzamides are particularly and notably safe to cereal crops, such as corn, rice and especially wheat, and their use as herbicides in cropland in which such crops are grown is particularly preferred. They may also safely be used, however, in many other crops, such as soybeans, peanuts, cotton, peas and related crops. The compounds are also useful for the control of unwanted vegetation is non-cropland, such as in fallow wheat land and the like. It is often convenient to apply herbicides in combination with other herbicides or with crop protection chemicals such as fungicides, insecticides and the like. The benzamides may conveniently be applied in the form of such combinations when it is desired to do so.

The following preparations and examples illustrate the invention further. The first group of preparations below illustrate the synthesis of a typical starting 2-propenoic acid.

Preparation 1

(2-ethyl-2-methylbutyryl)acetonitrile

To a suspension of 96 g. of sodium hydride, as a 50% dispersion in mineral oil, in 300 ml. of dry tetrahydrofuran was added, with stirring, 63 g. of acetonitrile and 114 g. of methyl 2-ethyl-2-methylbutyrate. The mixture was then heated gently to 60°–65° and allowed to reflux gently at that temperature overnight. It was then cooled to ice bath temperature, and 2-ml. portions of ethanol were added to decompose the remaining hydride. When the mixture did not foam on further ethanol addition, the mixture was evaporated under vacuum to dryness, and the residue was dumped into 4 liters of water. The aqueous mixture was extracted with hexane to remove the mineral oil, and it was then made acid to pH 2 and was extracted with two 1-liter portions of diethyl ether. The ether was dried over magnesium sulfate and evaporated under vacuum to obtain 122 g. of the desired acetonitrile.

Preparation 2

1-acetyl-1-ethyl-1-methylpropane

To the 122 g. of alkanoylacetonitrile obtained in Preparation 1 was added 1 liter of 12 N hydrochloric acid. The mixture was heated to reflux, and was stirred under reflux for 2 hours. It was then cooled and extracted with 1 liter of pentane. The organic layer was dried over magnesium sulfate and evaporated under vacuum at 35° to obtain 93 g. of crude product.

Preparation 3

1,1,1-trichloro-5-ethyl-2-hydroxy-5-methyl-4-oxoheptane

A 30 g. portion of the product of Preparation 2, 1-acetyl-1-ethyl-1-methylpropane, was combined with 38.4 g. of chloral and 36 ml. of acetic acid, and was stirred under reflux, under nitrogen, for 4 days. The solvent was then carefully removed under vacuum to obtain 39 g. of the crude product as an amber, viscous oil.

Preparation 4

5-ethyl-5-methyl-4-oxo-2-heptenoic acid

The product of the preparation immediately above was dissolved in 400 ml. of ethanol and brought to a boil. To it was quickly added 40 g. of potassium hydroxide in 360 ml. of water, and the temperature was held at 72° for 2 minutes. The mixture was then poured immediately into 1 liter of ice-water, and 50 g. of sodium chloride was added. The aqueous mixture was extracted with 1000 ml. of diethyl ether, and the aqueous layer was made acid with concentrated hydrochloric acid. It was then extracted 4 times with 500 ml. portions of dichloromethane, and the organic layers were combined, dried over magnesium sulfate and evaporated under vacuum to obtain 20 g. of the desired acid, as a mixture with 5-ethyl-2-hydroxy-5-methyl-4-oxoheptanoic acid, the presence of which was indicated by nuclear magnetic resonance signals, δ 4.35 (q, 1H); 2.6–3.8 (m, 2H).

The following examples illustrate the process of this invention.

EXAMPLE 1

6-(1-ethyl-1-methylpropyl)-3-pyridazinone

To the product mixture from Preparation 4 above was added 200 ml. of ethanol and 3.6 g. of hydrazine. The mixture was stirred under reflux for 3 days in a Pyrex flask exposed to a 300 watt sun-lamp. The lamp emitted light which was primarily of wave lengths between 200 and 800 mμ, and the lamp was placed 5 cm. from the wall of the flask. The mixture was then cooled and evaporated to an oil under vacuum, and the oil was purified by chromatography over 500 g. of silica gel, eluting with 1:1 ethyl acetate:dichloromethane. The product-containing fractions were combined and evaporated under vacuum to obtain a solid, which was crystallized from hexane to obtain 4.3 g. of the desired product, m.p. 97°–99°.

EXAMPLE 2

5-t-butyl-5-hydroxy-2-oxofuran

To 8.5 g. of pure 5,5-dimethyl-4-oxo-2-hexenoic acid in 150 ml. of diethyl ether was applied irradiation from a 300 watt sun-lamp. The solution was in a 500 ml. Pyrex flask, and the lamp was placed 5 cm. from the flask. The light emitted by the lamp was primarily of wave length 200 to 800 mμ. The irradiation was continued for about 18 hours. The mixture was then evaporated under vacuum to obtain 8.5 g. of the desired product as colorless crystals.

EXAMPLE 3

6-t-butyl-3-pyridazinone, hydrochloride

Seven g. of the furanone obtained in the example above was combined with 20 ml. of ethanol, 4.8 ml. of 12 N hydrochloric acid and 1.5 g. of hydrazine. The reaction was complete after 4 hours of stirring at reflux, but was allowed to continue for 2 days. The mixture was then cooled, and 200 ml. of ethyl acetate was added. The precipitate resulting was removed by filtration, and the filtrate was evaporated under vacuum to obtain a crystalline solid. About 75 ml. of ethyl acetate was added and the mixture was stirred and cooled to obtain 4.0 g. of crystalline product, m.p. 171°–173°. It was identified as the desired product by its nuclear magnetic resonance spectrum, obtained in DMSOd$_6$, which showed characteristic features at δ 1.26 (s, 9H, t-butyl); 6.82 (d, J=10 Hz, H5); 7.73 (d, J=10 Hz, H3).

EXAMPLE 4

6-(1-ethylcyclohexyl)-3-pyridazinone

To 14.0 g. of 4-(1-ethylcyclohexyl)-4-oxo-2-butenoic acid was added 100 ml. of ethanol and 4 g. of hydrazine. The mixture was stirred under reflux under a 300 watt sun-lamp in a 100 ml. Pyrex flask for 18 hours. The lamp was placed 5 cm. from the flask and emitted light of wave lengths primarily between 200 and 800 mμ. The mixture was then evaporated to dryness under vacuum, and to the residue was added 1000 ml. of diethyl ether. The ether solution was washed with 500 ml. of 0.1 N hydrochloric acid, 0.1 N sodium hydroxide and saturated sodium chloride solution, dried over magnesium sulfate and evaporated under vacuum to an oil. The oil was taken up in a little hexane and triturated to obtain a crystalline solid. The solid was recrystallized from ethyl acetate/hexane to obtain 0.15 g. of the desired product, m.p. 138°–140°. It was identified by its infrared spectrum, showing absorption bands at 1650 and 1675 cm.$^{-1}$, and by its mass spectroscopy spectrum, showing its molecular ion of mass 206.

The following preparations illustrate the use of the pyridazinones as intermediates for the preparation of pyridazinylbenzamide herbicides.

Preparation 5

3-chloro-6-(1-ethyl-1-methylpropyl)pyridazine

To 34 g. of 6-(1-ethyl-1-methylpropyl)-3-pyridazinone was added 175 ml. of phosphorus oxychloride, and the mixture was stirred under reflux for 30 minutes. It was then cooled, excess phosphorus oxychloride was removed under vacuum, and the residual oil was poured into ice water. The residue was made basic to pH 9 with ammonia, and triturated. The aqueous mixture so prepared was extracted with two one-liter portions of diethyl ether, and the combined organics were dried and evaporated under vacuum to obtain 35 g. of the desired product, identified by mass spectroscopy, which showed a molecular ion having a weight of 198.

Preparation 6

3-amino-6-(1-ethyl-1-methylpropyl)pyridazine

To the product obtained from the preparation immediately above was added 1000 ml. of liquid ammonia in a pressure vessel, and the mixture was heated at 200° for 50 hours. The mixture was cooled and the volatiles were allowed to evaporate, and the residue was dissolved in 500 ml. of denatured ethanol. The insoluble matter was removed and the solvent was evaporated under vacuum. The residue was purified by chromatography on a 700 g. silica gel column, using ethyl acetate as the eluting solvent. The product-containing fractions were combined and evaporated to obtain an oil which crystallized on standing. The yield was 24 g. of the desired product, m.p. 56°–58° after recrystallization from hexane.

Preparation 7

N-[6-(1-ethyl-1-methylpropyl)pyridazin-3-yl]-2,6-dimethoxybenzamide

A mixture of 21 g. of the product of the preparation immediately above and 23.5 g. of 2,6-dimethoxybenzoyl chloride was dissolved in 500 ml. of benzene, and the mixture was stirred under reflux overnight. The solvent was removed under vacuum, and to the residue was added a solution of 20 g. of potassium hydroxide in 500 ml. of ethanol. The mixture was stirred under reflux for 3 hours, cooled and evaporated under vacuum. To the residue was added 500 ml. of saturated sodium chloride solution, and the aqueous mixture was extracted 3 times with 500 ml. portions of diethyl ether. The organic layers were combined and dried over magnesium sulfate, and the solution was evaporated under vacuum. The crude product was then dissolved in 1000 ml. of diethyl ether and washed with 0.1 N hydrochloric acid. The organic layer was dried and evaporated under vacuum. The oil was treated with 300 ml. of water containing 5 g. of hydroxylamine hydrochloride and 1 liter of diethyl ether, and the 2-phase mixture was stirred for 1 hour. The organic layer was then separated and washed with 2 N sodium hydroxide, dried and evaporated under vacuum to obtain 23 g. of crude product, which was then dissolved in 500 ml. of ethanol containing 40 g. of potassium hydroxide. That mixture was stirred under reflux for 14 hours, cooled and evaporated under vacuum. A 1.5 liter portion of water was added, and the resulting suspension was filtered. The solids were dissolved in ethyl acetate, treated with charcoal and filtered. The filtrate was evaporated under vacuum to obtain a solid which was crystallized from benzene/hexane to obtain the desired product, m.p. 145°–147°.

I claim:

1. A process for preparing a pyridazinone of formula

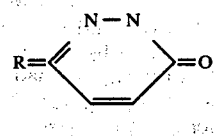

wherein
R is of the formula

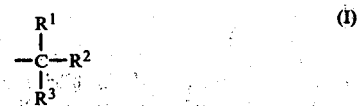

$R^1$ is $C_1$–$C_4$ alkyl;
$R^2$ and $R^3$ are independently $C_1$–$C_{13}$ alkyl, or halo-$C_1$–$C_{13}$ alkyl;
n is 0–4;
comprising irradiating a 2-propenoic acid of the formula

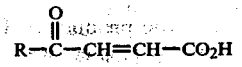

to form a furanone of the formula

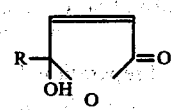

and reacting the furanone with hydrazine.

2. A process of claim 1 for preparing a pyridazinone wherein $R^2$ and $R^3$ are independently $C_1$–$C_4$ alkyl or halo-$C_1$–$C_4$ alkyl.

3. A process of claim 2 for preparing a pyridazinone wherein $R^2$ and $R^3$ are independently $C_1$–$C_4$ alkyl.

4. A process of claim 1 for preparing a pyridazinone wherein $R^1$ is not branched.

5. A process of claim 3 for preparing a pyridazinone wherein $R^1$ is not branched.

6. A process of claim 5 for preparing a pyridazinone wherein $R^2$ and $R^3$ are not branched.

7. A process of claim 1 for preparing a pyridazinone wherein R is t-butyl.

8. A process of claim 1 for preparing a pyridazinone wherein R is 1-ethyl-1-methylpropyl.

9. A process of any one of claims 1–8 wherein the 2-propenoic acid is irradiated with light which is substantially in the range of from about 100 to about 1000 mµ wave length.

10. A process of claim 9 wherein the reaction with hydrazine is in the presence of hydrochloric acid.

11. A process of claim 10 wherein the reaction with hydrazine is in the presence of a lower alkanol.

12. A process of claim 11 wherein the reaction with hydrazine is in the presence of ethanol.

* * * * *